United States Patent [19]

Wetterlin et al.

[11] 4,188,986

[45] Feb. 19, 1980

[54] MICROSAMPLER

[76] Inventors: Leif Sune V. Wetterlin, Edvard Ols vag 4, 230 42 Tygelsjo; Bertil G. Frank, V. Karaby (pl 289), 240 23 Dosjebro, both of Sweden

[21] Appl. No.: 901,066

[22] Filed: Apr. 28, 1978

[30] Foreign Application Priority Data

May 6, 1977 [SE] Sweden .................................. 7705278

[51] Int. Cl.² ............................................ B65B 43/50
[52] U.S. Cl. ...................................... 141/130; 65/112; 128/768; 422/64
[58] Field of Search ............. 141/1, 11, 130, 183–190, 141/98, 31; 422/64, 65; 128/2 F; 65/112

[56] References Cited

U.S. PATENT DOCUMENTS

| 3,593,761 | 7/1971 | Lorenz ................. 141/190 |
| 3,807,959 | 4/1974 | Russell et al. ......... 141/130 |
| 3,880,211 | 4/1975 | Gess ................... 141/183 |

FOREIGN PATENT DOCUMENTS 348291 8/1972 Sweden.
354962 2/1973 Sweden.

Primary Examiner—Houston S. Bell
Attorney, Agent, or Firm—Laurence R. Brown

[57] ABSTRACT

A microsampler sampling a catheter connected, for example, to a mouse artery has a stepwise operated cylinder presenting spaced mounting tubes holding capillaries which are coupled sequentially to the catheter for capillary transfer and measurement.

5 Claims, 3 Drawing Figures

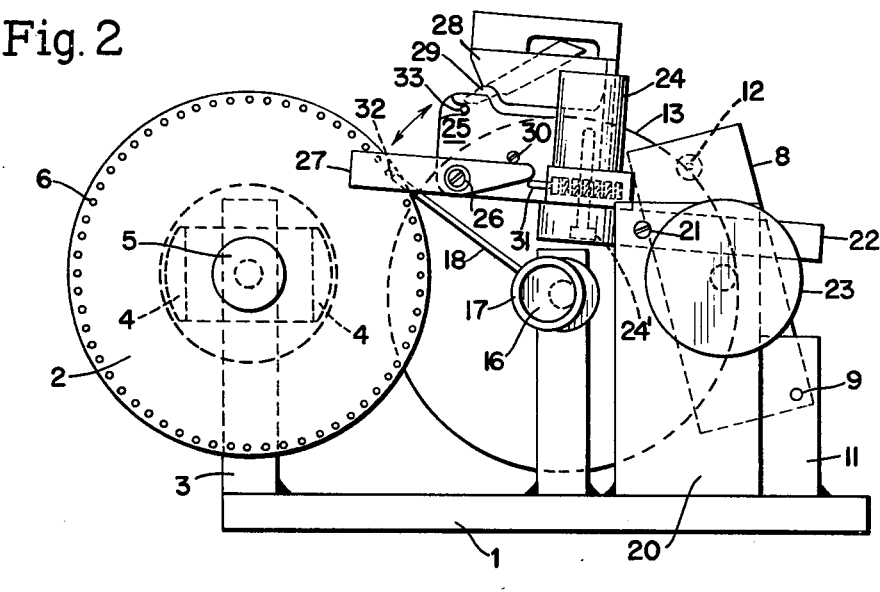
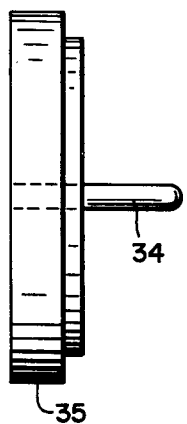
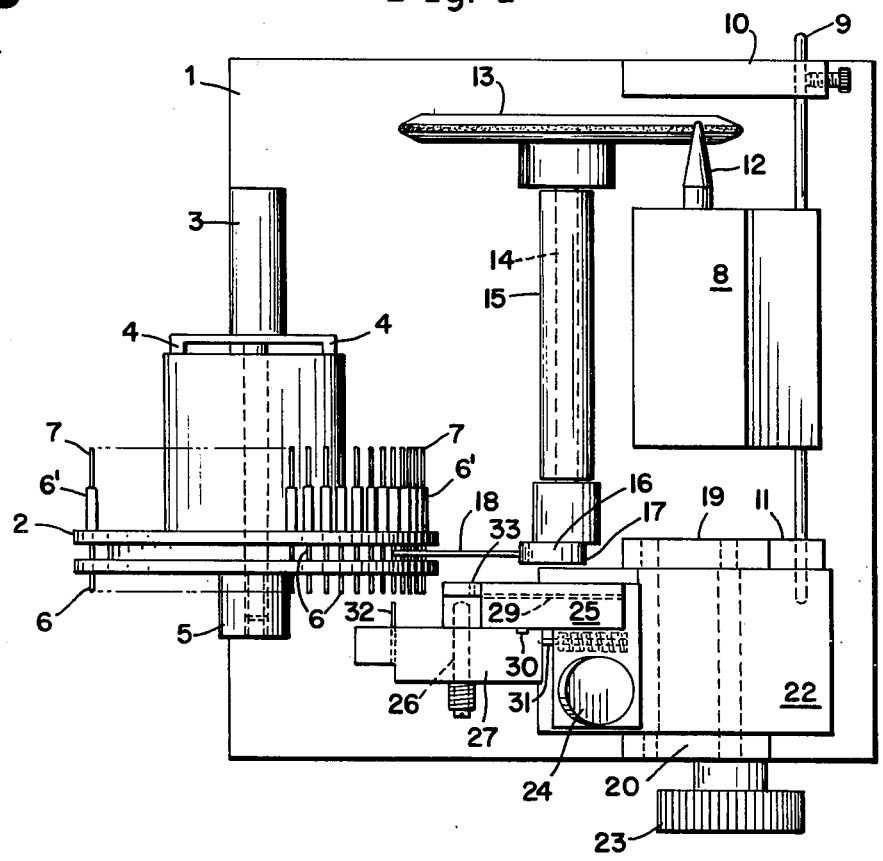

MICROSAMPLER

The present invention relates to a microsampler for rapid collection of a number of small volume samples of liquid delivered to the microsampler through a thin catheter. The order of magnitude of the smallest samples is 2–6 microliters.

The background for this invention was the desire to determine with great precision the cardiac output in the mouse, which in the future expectedly may grow more important as laboratory animal. Because the average weight of a mouse is 25 g and its total blood volume is 2,5 ml, it has not been possible to use conventional sampling methods for men, dogs or rats.

This is according to the invention attained in that the microsampler according to the invention is characterized on the one hand by a stepwise operated cylinder, provided with a ring of axially arranged capillaries with a separation corresponding to the steps of the cylinder, on the other hand by means for keeping the catheter in position close to and opposite each advanced capillary.

In a practical embodiment the cylinder is provided with mounting tubes for the capillaries and an advancing arm driven by an eccentric drive shaft arranged to cooperate stepwise advancing with the mounting tubes.

To ensure a controlled rotation an adjustable braking device cooperates with the cylinder.

The sampling cylinder can be provided with 60 evenly distributed mounting tubes. A suitable step-feeding speed may be 2 cycles per second.

Before sampling the catheter connected with a liquid source (for example the mouse), should be blocked. Immediately before sampling the catheter shall be open ended (preferably cut off) and at once be placed in exact position opposite a capillary. This is according to the invention attained in that the catheter is passed through a feeding tube in an arm, which is pivotable from a stand-by position with the catheter extending out of the feeding tube in position to be cut off by a knife mounted on the device, to an operation position, in which the cut-off catheter end extending out of the feeding tube is in close vicinity of a capillary on the cylinder.

It is important to note that the microsampler according to the invention can be used not only for determination of cardiac output in small animals but also in many other areas where rapid sampling with an absolute minimum of liquid spillage is desired.

The invention will be further described below, reference being made to the attached drawing, in which FIGS. 1 and 2 in a plan view and a side view respectively show a microsampler according to the invention and FIG. 3 shows a separate loading plate for the installation of the microsampler.

On a foundation 1 a sampling cylinder 2 is rotatably journalled in a stand 3, which is provided with brake blocks 4 in order to achieve a suitable friction resistance for the cylinder 2. This cylinder 2 is kept in position on its axle by a dismountable nut 5.

The cylinder 2 has a number of mounting tubes 6, in the actual case sixty tubes, which are used on the one hand as holders for capillaries 7, on the other hand as parts in the stepwise operated mechanism for the cylinder, which mechanism can be of the following design.

An electric motor 8 is pivoted on an axle 9 attached to stands 10 and 11 in the foundation 1. An outgoing drive axle 12 of the motor 8 is conical and interacts with a drive wheel 13, which is provided with a rubber ring and whose axle 14 is pivoted in a stand 15 on the foundation 1. At the end of the axle 14 opposite the drive wheel 13 there is an excenter wheel 16, on which is mounted a ring 17 having an advancing arm 18 cooperating with the mounting tubes 6 in such a way that with each revolution of the axle 14 the cylinder 2 will be advanced one step, i.e. 1/60 of a whole revolution in the actual case. By adjustment of the position of the conical drive axle 12 relative to the drive wheel 13 a suitable stepwise operational speed can be achieved, in the actual case two cycles per second.

Between stands 19 and 20 on the foundation 1 there is a substantially horizontal plate 22 which is movable around an axle 21. The stands 19 and 20 can be squeezed together with a screw 23 in order to fix the position of the plate 22.

A unit consisting of parts as mentioned below can be pivoted in the plane of the plate 22 around an axle 24. The position of the unit can be fixed with a screw 24.

The unit consists of a central part 25, an arm 27 pivotally attached thereto by an axle 26 and a knife-bracket 28 with a knife 29 resiliently attached to the central part 25. The arm 27 can be moved from a substantially vertical position into a shown, substantially horizontal position against an abutment 30 passing a stabilizing, spring-loaded pin 31. In the arm 27 a feeding tube 32 is inserted, which in the vertical position of the arm will be opposite a hole 33 in the central part 25.

Installation of the microsampler is carried out in the following way: The cylinder 2 is removed and put on a separate loading plate 35 (FIG. 3) with its axle spindle 34 extending into the hole of the cylinder. Capillaries 7 (so called microcaps) with a volume of 20 $\mu$l each are inserted into the mounting tubes 6 until they reach the plate 35 for obtaining well-defined positions, which are maintained by silicon rubber pieces 6' on the tubes 6. After loading, the cylinder 2 is again placed on its axle.

The arm 27 is pivoted into a vertical position against the abutment, so that the feeding tube 32 is in line with the hole 33. Through this tubular opening a thin plastic catheter is inserted. This catheter is connected to a test object, in this case to an artery of a mouse, whereas the other end of the catheter (protruding from the hole 33) is blocked.

Provided that after loosening of the screws 23 and 24 the feeding tube 32 earlier has been put into correct position (for example 0,5–0,6 mm from a capillary 7) with the arm 27 in the shown operating position, the motor 8 may be started, so that the excentrically journalled advancing arm 18 starts the stepwise operation of the capillaries in front of the operational position to be of the feeding tube 32 with the arm 27 in the horizontal position.

Before starting the sampling, the catheter connected with the test object is cut by the knife 29 by compression of the knife bracket 28. The arm 27 is rapidly pivoted into the shown operational position, where it is locked by the abutment 30 and the pin 31.

Liquid from the test object, i.e. blood from the mouse, is now transferred to the step-wise advanced capillaries 7 by the capillary force in a constant amount, and no liquid will be spilled due to the rapid stepwise advancement. The distance between the catheter tip and each respective capillary is 0.2–0.3 mm which is necessary for the functioning of the capillary force.

The liquid column in each capillary 7 can after the sampling be measured in a microscope with an accuracy of a tenth of a millimeter. In this way it will be possible to determine the cardiac output of the mouse.

Many modifications are possible. For example the mechanism for the stepwise operation can be modified, which also goes for the whole arrangement for the mounting, cutting and positioning of the catheter from the test object. The inventive idea is the technique to make use of stepwise advanced capillaries for collecting very small liquid volumes.

We claim:

1. A microsampler device for transfer of small volume samples by capillary action, comprising in combination, presentation means presenting at least one measuring tube of microsampling capacity of the order of 20ml in volume and having an open ended capillary tube precisely in position past a transfer station, means presenting at the transfer station in registration with the open ended measuring capillary tube when moved therepast, a catheter coupled to a fluid source terminating in a capillary sampling tube open end presenting fluid from the source and located to register at a distance in the order of less than one mm from the measuring tube open end, and means moving the presentation means and measuring tube rapidly past the transfer station to transfer liquid from the capillary tube open end into the measuring tube open end by capillary flow.

2. A microsampler as defined in claim 1 including cutting means for cutting said sampling tube to a predetermined length registering at said distance.

3. A microsampler as defined in claim 2 including means for presenting said sampling tube cut off at said length by said cutting means to said measuring tube with a step-by-step mechanism presenting a plurality of the measuring tubes to registration position.

4. A microsampler as defined in claim 3 wherein said step-by-step means moving the plurality of measuring tubes past said sampling tube at said station has motivating means passing the tubes rapidly enough that the only liquid taken from the sampling tube is that transferred to the measuring tubes and thus no liquid is spilled from the sampling tube.

5. A microsampler as defined in claim 1 wherein said catheter is connected to an artery of a mouse as a fluid source.

* * * * *